(12) United States Patent
Uludağ et al.

(10) Patent No.: US 11,493,474 B2
(45) Date of Patent: Nov. 8, 2022

(54) MOBILE HAND-HELD DEVICE WITH REUSABLE BIOSENSOR CARTRIDGE

(71) Applicant: TUBITAK, Ankara (TR)

(72) Inventors: Yildiz Uludağ, Kocaeli (TR); Mehmet Yağmur Gök, Kocaeli (TR); Serkan Barut, Kocaeli (TR); Veysi Cansu, Kocaeli (TR)

(73) Assignee: TUBITAK, Ankara (TR)

( * ) Notice: Subject to any disclaimer, the term of this patent is extended or adjusted under 35 U.S.C. 154(b) by 982 days.

(21) Appl. No.: 16/314,395

(22) PCT Filed: Jul. 1, 2016

(86) PCT No.: PCT/IB2016/053975
§ 371 (c)(1),
(2) Date: Dec. 29, 2018

(87) PCT Pub. No.: WO2018/002693
PCT Pub. Date: Jan. 4, 2018

(65) Prior Publication Data
US 2019/0204260 A1    Jul. 4, 2019

(51) Int. Cl.
| G01N 27/327 | (2006.01) |
| G01N 33/487 | (2006.01) |
| G01N 27/416 | (2006.01) |
| G01N 35/00 | (2006.01) |

(52) U.S. Cl.
CPC ....... *G01N 27/3277* (2013.01); *G01N 27/416* (2013.01); *G01N 33/48785* (2013.01); *G01N 35/00732* (2013.01); *G01N 2035/00742* (2013.01); *G01N 2035/00891* (2013.01)

(58) Field of Classification Search
None
See application file for complete search history.

(56) References Cited

U.S. PATENT DOCUMENTS

| 5,200,052 | A | * | 4/1993 | Ishibashi | G01N 35/08 204/409 |
| 2010/0313688 | A1 | * | 12/2010 | Hiltbrand | G01N 35/1072 73/864.91 |
| 2013/0214040 | A1 | | 8/2013 | Beerling et al. | |
| 2013/0331675 | A1 | * | 12/2013 | Batman | G01N 33/48785 600/365 |
| 2014/0017709 | A1 | * | 1/2014 | Lowe | G01N 33/5438 435/7.92 |
| 2015/0198594 | A1 | * | 7/2015 | Williams | G01N 33/56916 435/287.2 |
| 2017/0191956 | A1 | * | 7/2017 | Kuwabara | B01L 3/502707 |

FOREIGN PATENT DOCUMENTS

| EP | 2508867 A1 | 10/2012 |
| WO | 2015155665 A1 | 10/2015 |

* cited by examiner

*Primary Examiner* — Matthew D Krcha
(74) *Attorney, Agent, or Firm* — Bayramoglu Law Offices LLC

(57) ABSTRACT

This invention relates to a handheld mobile device which can analyze and measure whole blood, serum, urine or analytes which contain target agents such as mycotoxin, aflatoxin or cholera etc. with a easy to use reusable cartridge consisting of a cartridge head and cartridge body. The cartridge comprises four syringes, one of which being detachable. A waste reservoir is integrated with the syringes.

15 Claims, 4 Drawing Sheets

MOBILE HAND-HELD DEVICE WITH REUSABLE BIOSENSOR CARTRIDGE

CROSS REFERENCE TO THE RELATED APPLICATIONS

This application is the national phase entry of International Application No. PCT/IB2016/053975, filed on Jul. 1, 2016, and the entire contents of which are incorporated herein by reference.

TECHNICAL FIELD

This invention relates to a mobile handheld device with reusable and replaceable cartridge technology for quantitatively determining an analyte in a fluid sample, and more specifically using a method called Real-time Electrochemical Profiling (REP™) for detecting biological compounds such as disease protein/genomic biomarkers or chemical agents such as aflatoxins or mycotoxins etc.

BACKGROUND

Biosensors have uses in medical diagnostics, environmental pollutant detection, food and pharmaceutical industries, biological warfare agent detection etc. Devices used for these applications are usually large costly and requires sample transportation to a laboratory. Sometimes procedures include the use of several devices and a central laboratory to get results. These type of analyses may be costly and the quality of the measurement can be affected due to the long distances the sample has to travel, which may have inadequate conditions. This leads to the necessity of onsite detection by means of portable biosensor devices.

The oldest biosensors date back to the 1950s. They were used for oxygen monitoring. By 1980s electrochemical detectors were miniaturized, exhibiting good sensitivity and selectivity. An electrochemical biosensor causes a change in an electrical signal using a specific binding material, such as protein, deoxyribonucleic acid ("DNA"), viruses, bacteria, cells, and tissues, and a sensor surface, thereby quantitatively or qualitatively analyzing and testing biomolecules. Detection of a biological material requires a complex process for processing, reaction, and analysis of a reagent. Although the process varies according to an analysis method and the type of the material, a biosensor generally detects a biological material through a complex combination of processes such as filtering, metering, mixing, transport, reaction and washing. Thus, according to conventional art, detection of a biological material is manually performed in respective laboratories using a variety of equipment. Mobile biosensor devices are usually composed of a sensor where the detection—reaction takes place, a transducer (electrochemical, optical or piezoelectric) which translates the signal, an electronic part which processes the signal from the transducer and shows the results to the user.

The mobile hand held device BiSens employs a microfluidic mechanism, bringing an innovative and simple solution with an easy to use cartridge system which includes an on board biosensor and does not need to be calibrated by the user. The aim is to provide mobility and repeatable quality while staying close to the high quality measurements of the laboratories. The cost of the measurement is also reduced significantly while providing constant quality measurement convenience on site.

SUMMARY

The hand-held apparatus consists of a cartridge loading mechanism, a single use all-in-one cartridge with RFID label and a movable syringe with mount for user sample placement, motors and pistons for microfluidic action, a micro potentiostat circuit, RFID reader for cartridge detection, a capacitive touch display, a control unit for signal processing and recording, a battery unit for the power of the overall system and an optional adapter for external power or operation without battery. The device works with temperature compensation and has been calibrated to work between 15° C. and 35° C.

The cartridge consists of three stationary syringes and one detachable syringe for sample placement. The biosensor is integrated with the cartridge. The cartridge also houses a waste reservoir. We call this concept an all-in-one cartridge. The fluidics from the syringes, the reaction and waste chamber is connected with microfluidic channels. The fluids are routed from the syringes to the flow cell where the electrodes are housed and then finally end up in the waste chamber.

The integrated biosensor chip consists of specially designed electrodes formed on a glass/silicon oxide substrate (PCT application no: PCT/IB2015/052479). It can detect various analytes based on the bio-recognition elements used for the biological assay. Waste is also integrated on the cartridge. The cartridge is completely sealed including the detachable syringe. When the measurement is started by the user, the syringes are moved by the pistons that are actuated by micro stepper motors.

To start a measurement, the user will first place the cartridge in its slot and then select 'start' from the menu on the touchscreen, then the apparatus will read the RFID information of the cartridge and automatically run the embedded protocol. After the measurement is complete, the result is shown to the user on the graphic screen either by means of a plot, in the form of analyte concentration or in the form of yes or no result.

BiSens with its integrated biosensor chip, waste chamber, RFID tag cartridge system will save the user from cleaning procedures as this is done automatically. All the user has to do for a new measurement is to throw away the old cartridge and slot in the new one. The RFID technology integrated into the apparatus makes test preparation obsolete as the protocol is automatically read by the device.

BRIEF DESCRIPTION OF THE DRAWINGS

The invention is explained in greater detail in the following referred diagram and figures.

Figure 1:
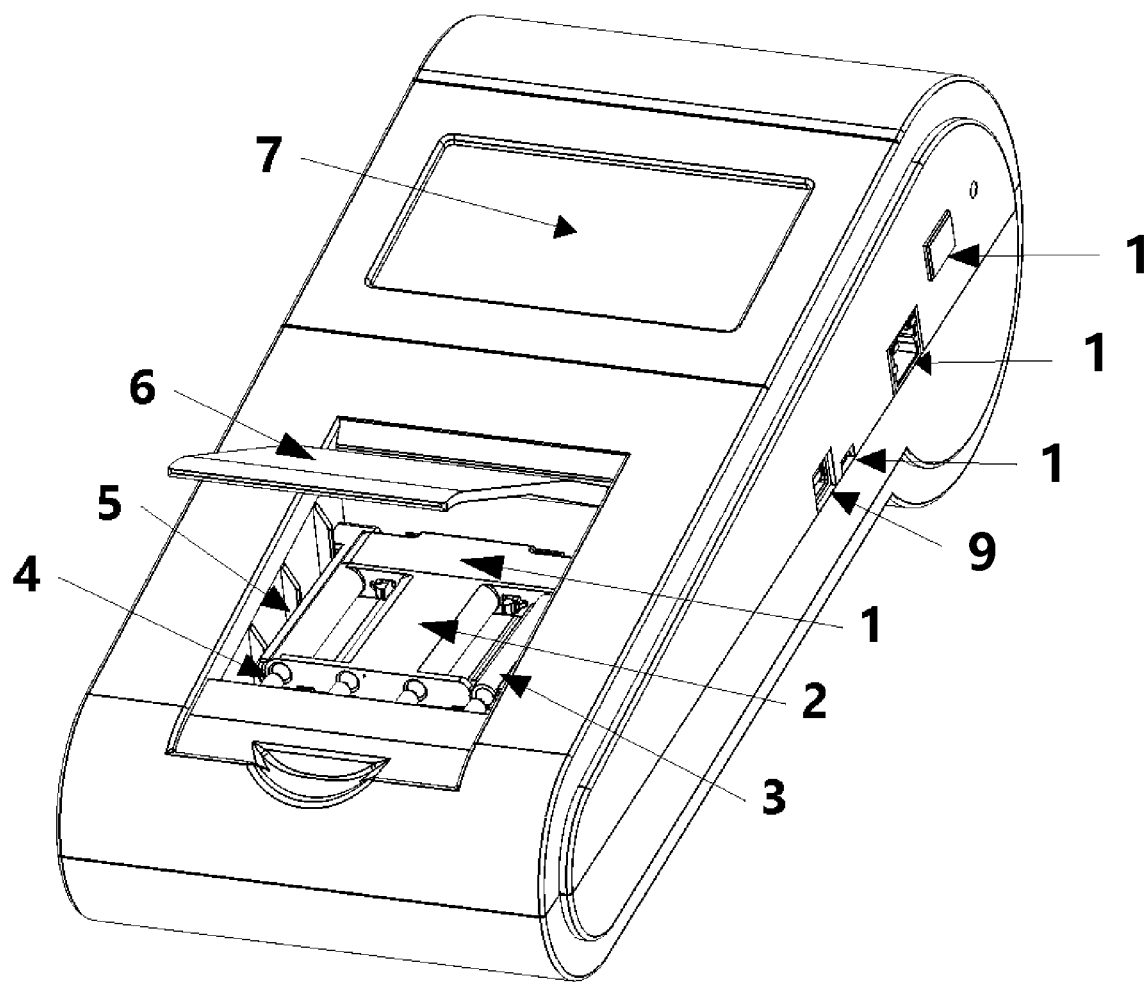
FIG. 1 is a perspective view of the apparatus from above.

Features of the embodiments identified by reference numerals in the drawings:

1. Cartridge head
2. Cartridge body
3. User detachable syringe
4. Metal piston
5. Cartridge slot
6. Cartridge lid
7. Capacitive touch screen
8. Electric motor
9,10. USB ports
11. Ethernet port 12. Power socket
13. Piston head
14. Syringe sealing ring
15. Sensor slot of the biosensor chip
16. Biosensor chip
17, 17a. Two-sided adhesive sticker
18. Cover of the biosensor chip
19. Metal rods
20, 20a. Microswitch
21. Microfluidic channels
22. Inlet channel
23. Outlet channel
24. Waste deposit opening
25. Syringe head slot
26. Waste reservoir
27, 27a. Motor bracket
28. Bottom chassis
29. Inlet opening
30. Outlet opening

DETAILED DESCRIPTION OF THE EMBODIMENTS

The electrochemical detection apparatus shown in the figures, which includes a set up comprised of an apparatus housing a cartridge, electrical and mechanical syringe pump system, electrochemical biosensor attached to the cartridge, a cartridge comprised of a cartridge body, housing syringes and a fluidic waste deposit, and a cartridge head housing microfluidic channels and a biosensor mount.

FIG. 1 is an overall schematic view of the electrochemical hand held device. A cartridge comprised of two elements; cartridge head (1) and cartridge body (2). There is a user detachable syringe (3) for sample placement. The cartridge is placed to its slot (5) by the user. The cartridge lid (6) is then closed. The protocol is started by the user from the capacitive touchscreen (7). A metal piston (4) injects the appropriate fluid with the help of an electric motor (FIG. 3-8). If required the results can be transferred to a PC by the user by means of a USB or network cable using the appropriate ports (9,10,11). The device also can be integrated to a lab or hospital system if requested by the customer with the help of the Ethernet port (11). If desired the apparatus can be powered on by an external adapter by inserting the power cable into the power socket (12).

Figure 2:
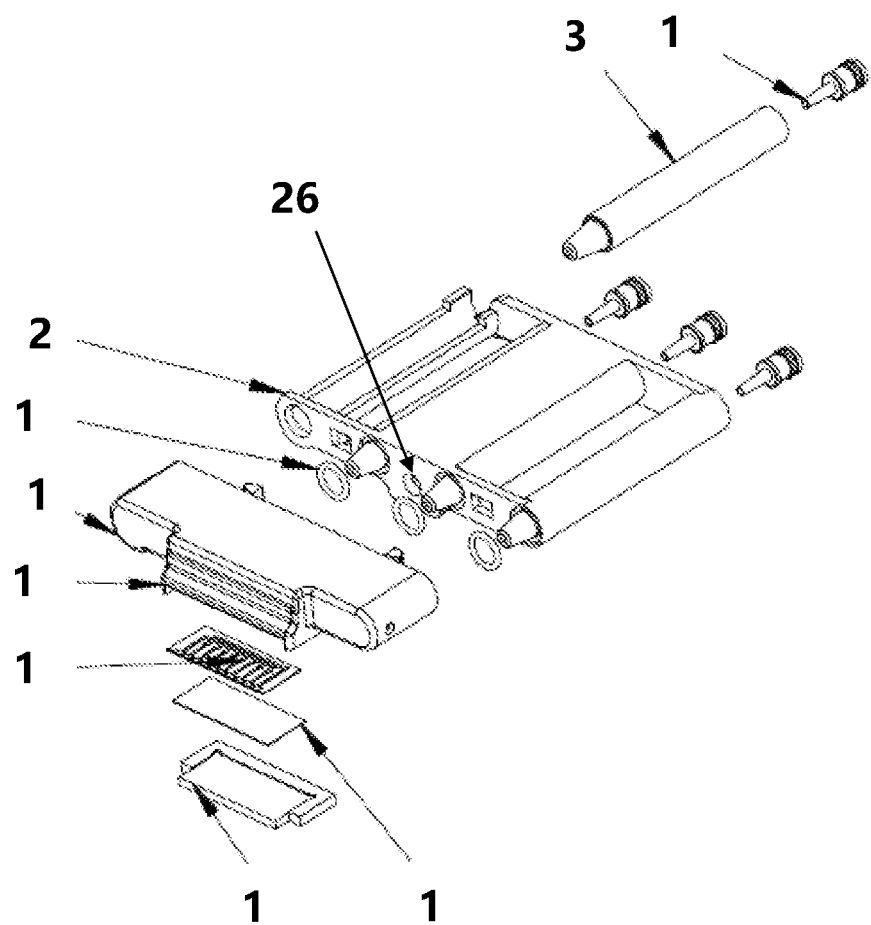
FIG. 2 is an exploded perspective view of the cartridge, taken from above.

FIG. 2 shows parts of the cartridge. The cartridge is made up of two main pieces; the main cartridge body (2) and cartridge head (1). (3) is the user fillable syringe with the piston head (13). The syringe sealing ring (14) is used between the cartridge head (1) and cartridge main body (2) to prevent any fluidic leak. (15) is the sensor slot of the biosensor chip (16). (17) is an adhesive stick used to bond the biosensor chip (16) and its cover (18). The waste reservoir (26) integrated into the midst of the cartridge body (2) housing syringes in such a way that there are two syringes on the left and right side of the waste reservoir is connected to the outlet channel (FIG. 5-23), from which all consumables and waste fluidics leave the biosensor chip (FIG. 5-16), through the waste deposit opening (FIG. 5-24) on the cartridge head (1).

Figure 3:
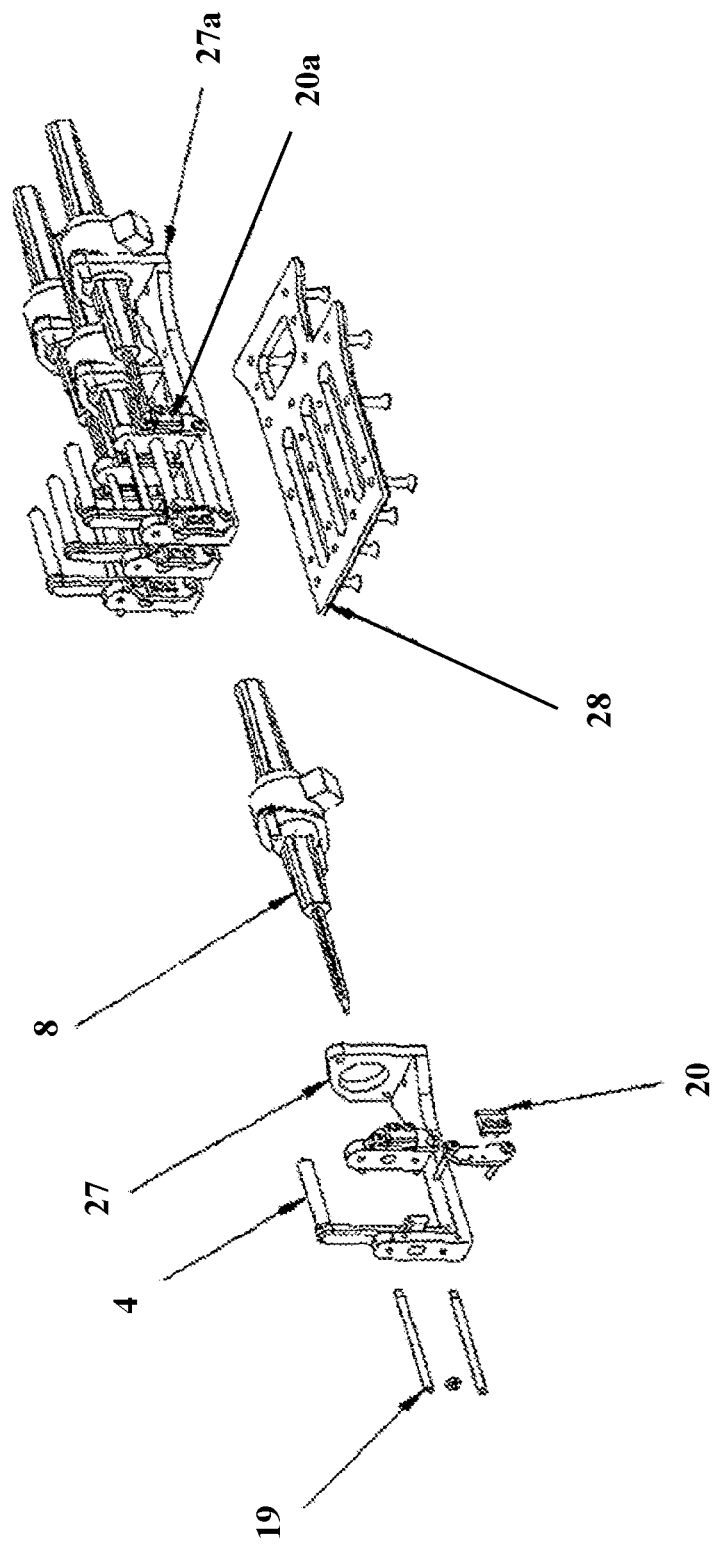
FIG. 3 is an exploded perspective view of the syringe pump mechanism, taken from above.

FIG. 3 is a perspective view from above showing the details of the electro-mechanical piston system. It is configured as a reverse pull-push system. The electrical motor (8) pulls the piece acting as a piston (4). The action of the piston is guided by two metal rods (19) to ensure rigidness of the motion. The pull or push motion is controlled by means of two micro switches (20, 20a). The motors are installed on the motor bracket (27a) and then it is placed on the bottom chassis (28) to install it into the apparatus.

Figure 4:
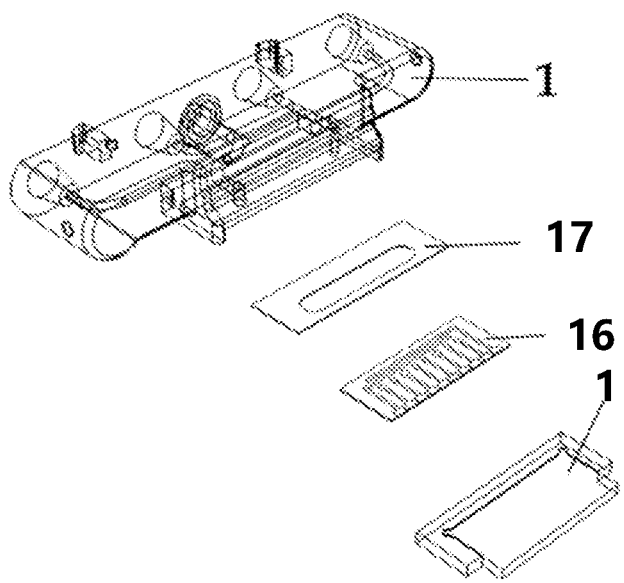
FIG. 4 is a perspective view of the cartridge head from above.

FIG. 4 is a detailed perspective view from above of the cartridge head. (1) is the cartridge head. Two-sided adhesive sticker (17a) with elliptic opening in the midst of which not only servesto bond the biochip (16) to the cartridge head (1), but also to form the thin flow cell as a result of the spacing between the cartridge head (1) and the biochip (16).

Figure 5:
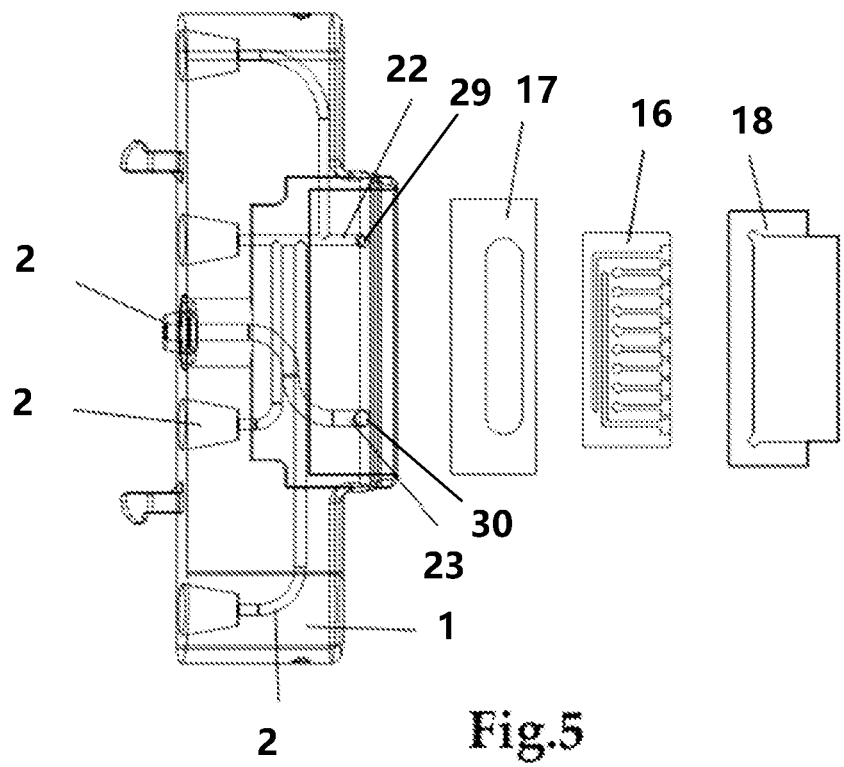
FIG. 5 is a top view of the cartridge head.

FIG. 5 is a detailed top view of the cartridge head (1) and the biochip (16). The microfluidic channels (21) are clearly seen in the transparent drawing of the cartridge head (1). Two openings of the cartridge head (1) connected to the inlet channel (22) and outlet channel (23) respectively constitutes the inlet opening (29) and outlet opening (30) of the flow cell, allowing fluid transportation. The fluidics enter the flow cell from the inlet channel (22) and leave the flow cell from the outlet channel (23) through the waste deposit opening (24). The syringe head slot (25) on the cartridge head (1) allows for tight mounting of the syringes.

What is claimed is:

1. A mobile hand-held device, comprising:
    a cartridge, wherein the cartridge is a coupled two piece click-fit cartridge including a cartridge head and cartridge syringes, wherein
    a biosensor chip having a biosensor is integrated to the cartridge head for measuring an electrical signal generated by a reaction,
    the cartridge head has microfluidic channels arranged to provide fluid and sample transportation to the biosensor chip,
    a two-sided adhesive layer with an opening therethrough, wherein the biosensor chip is integrated to the cartridge head with the two-sided adhesive layer bonding the biosensor chip to the cartridge head,
    the cartridge syringes are made up of four syringes including a single fully detachable and pre-mounted syringe for sample insertion,
    an RFID tag is placed on the cartridge, wherein all information related to the cartridge and a protocol required to run a suitable analysis procedure for a desired measurement is stored on the RFID tag;
    a swinging hinge cartridge slot for housing the coupled two piece click-fit cartridge,
    a potentiostat circuit to process and convert signals from the biosensor to a suitable format to be handled by a main processing unit,
    an RFID reader unit configured to read the information of the cartridge and the protocol wirelessly from the cartridge,
    the main processing unit for processing data from the RFID, the potentiostat circuit, and a capacitive touch display,
    the capacitive touch display for enabling a user to control the mobile hand-held device and to view results,
    a battery to power the mobile hand-held device; and
    a waste reservoir, wherein waste fluidics are deposited in the waste reservoir, and the waste reservoir is connected to an outlet channel through a waste deposit opening on the cartridge head such that the waste reservoir is integrated with the cartridge syringes.

2. The mobile hand-held device according to claim 1, wherein the single detachable and pre-mounted syringe is configured to be filled by a user with a sample fluid to be analyzed.

3. The mobile hand-held device according to claim 1, wherein the microfluidic channels connect the cartridge syringes to a flow cell and the flow cell to the waste deposit.

4. The mobile hand-held device according to claim 3, wherein the biosensor is integrated to the cartridge head under the flow cell, and has a surface with electrodes facing directly into the flow cell.

5. The mobile hand-held device according to claim 1, wherein the RFID tag is attached under the cartridge for cartridge and protocol recognition.

6. The mobile hand-held device according to claim 1, wherein the cartridge is configured to be placed into the mobile hand-held device by sliding the cartridge down the swinging cartridge slot.

7. The mobile hand-held device according to claim 1, wherein the cartridge is locked to the mobile hand-held device by applying a slight downward force and the slot being locked by a mechanical mechanism.

8. The mobile hand-held device according to claim 1, wherein the fluidics in the cartridge syringes are pumped by means of a piston actuated by electrical stepper motors.

9. The mobile hand-held device according to claim 8, wherein the piston and the electrical motors are integrated together under the cartridge slot.

10. The mobile hand-held device according to claim 9, wherein the piston is guided by two metal rods.

11. The mobile hand-held device according to claim 1, wherein the RFID reader unit is disposed under the cartridge slot.

12. The mobile hand-held device according to claim 11, wherein the RFID reader is connected to the main processing unit for data reading and processing.

13. The mobile hand-held device according to claim 1, wherein the potentiostat is connected to the biosensor.

14. The mobile hand-held device according to claim 1, wherein the capacitive touch display is used to control and view results from the mobile hand-held device.

15. The mobile hand-held device according to claim 1, wherein the opening of the adhesive layer, the cartridge head, and the biosensor chip define a thin flow cell between the cartridge head and the biosensor chip.

* * * * *